United States Patent [19]

Feiring

[11] Patent Number: 5,333,614
[45] Date of Patent: Aug. 2, 1994

[54] MEASUREMENT OF ABSOLUTE VASCULAR FLOW

[76] Inventor: Andrew J. Feiring, 4454 N. Murray Ave., Milwaukee, Wis. 53211

[21] Appl. No.: 952,428

[22] Filed: Sep. 28, 1992

[51] Int. Cl.$^5$ .............................................. A61B 8/06
[52] U.S. Cl. ............................. 128/662.06; 128/661.1
[58] Field of Search .................. 604/53, 109, 101–102; 128/662.06, 692

[56] References Cited

U.S. PATENT DOCUMENTS

| | | | |
|---|---|---|---|
| 3,173,418 | 3/1965 | Baran | 604/101 |
| 4,423,725 | 1/1984 | Baran et al. | 604/43 |
| 4,610,662 | 9/1986 | Weikl et al. | 604/53 |
| 4,636,195 | 1/1987 | Wolinsky | 604/53 |
| 4,733,669 | 3/1988 | Segal | 128/662.06 |
| 4,856,529 | 8/1989 | Segal | 128/662.06 |
| 4,869,263 | 9/1989 | Segal et al. | 128/692 |
| 4,947,852 | 8/1990 | Nassi et al. | 128/662.06 |
| 5,041,084 | 8/1991 | De Vries et al. | 604/169 X |
| 5,046,503 | 9/1991 | Schneiderman | 128/662.06 X |
| 5,078,148 | 1/1992 | Nassi et al. | 128/662.06 |
| 5,226,421 | 7/1993 | Frisbie et al. | 128/662.06 X |

FOREIGN PATENT DOCUMENTS

| | | |
|---|---|---|
| 2513868 | 10/1975 | Fed. Rep. of Germany . |
| 3806458 | 9/1989 | Fed. Rep. of Germany . |
| 85/02779 | 7/1985 | PCT Int'l Appl. . |
| 721110 | 3/1980 | U.S.S.R. . |
| 1228821 | 6/1981 | U.S.S.R. . |
| 2219510 | 12/1989 | United Kingdom . |

OTHER PUBLICATIONS

Segal, Jerome, et al, "Instantaneous and Continuous Cardiac Output Obtained with a Doppler Pulmonary Artery Catheter", *JACC*, vol. 13, No. 6, May 1989:1382–92.

Segal, Jerome, et al, "Instantaneous and Continuous Cardiac Output in Humans Obtained with a Doppler Pulmonary Artery Catheter", *JACC*, vol. 16, No. 6, Nov. 15, 1990:1398–407.

Bing, Richard J., et al, "Techniques to Measure Coronary Blood Flow in May", American Journal of Cardiology, vol. 29, Jan. 1972:75–80.

Benchimol, A., et al, "New Method to Measure Phasic Coronary Blood Velocity in Man", *American Heart Journal*, vol. 81, No. 1, Jan. 1971:93–101.

Cole, James S., et al, "The Pulsed Doppler Coronary Artery Catheter: Preliminary Report of a New Technique for Measuring Rapid Changes in Coronary Artery Flow Velocity in Man", *Circulation*, vol. 56, No. 1, Jul. 1977:18–25.

Sibley, David H., et al, "Subselective Measurement of Coronary Blood Flow Using a Steerable Doppler Catheter", *JACC*, vol. 8, No. 6, Dec., 1986:1332–40.

Wilson, Robert F., et al, "Transluminal, Subselective Measurement of Coronary Artery Blood Flow Velocity and Vasodilator Reserve in Man", *Circulation*, vol. 72, No. 1, Jul. 1985:82–92.

(List continued on next page.)

*Primary Examiner*—Francis Jaworski
*Attorney, Agent, or Firm*—Haugen and Nikolai

[57] ABSTRACT

A vascular flow measurement catheter device for measuring total volumetric flow through a vessel includes a flow-measurement catheter having a full flow lumen of known cross sectional geometry provided with a relatively short distal measurement segment with inlet and outlet ports positioned to carry the full flow of the vessel in the manner of a segment of the vessel itself when the outer catheter is positioned in the vessel of interest. An ultrasonic transducer system is mounted in the flow-measurement catheter for communicating the velocity of the fluid in the measurement segment of the full flow lumen and for determining the total volumetric flow. An obturator catheter is provided in coaxial relation to the lumen of the flow-measurement catheter and adapted to travel along and within or without the full flow lumen of the measurement catheter to function to shut off the flow through the measurement catheter when advanced over inlet or outlet ports of the measurement catheter.

25 Claims, 3 Drawing Sheets

OTHER PUBLICATIONS

Kern, Morton J., "A Simplified Method to Measure Coronary Blood Flow Velocity in Patients: Validation and Application of a Judkins-style Doppler-tipped Angiographic Catheter", *American Heart Journal*, vol. 120, No. 5, Nov., 1990:1202–12.

Ofili, Elizabeth, et al, "Detection of Coronary Collateral Flow by a Doppler-tipped Guide Wire During Coronary Angioplasty", *American Heart Journal*, vol. 122, No. 1, Part 1, Jul. 1991:221–25.

Wright, Creighton, et al, "A Method for Assessing the Physiologic Significance of Coronary Obstructions in Man in Cardiac Surgery", *Circulation*, vol. 62, Suppl. 1, Aug. 1980:I-111–I-115.

MEASUREMENT OF ABSOLUTE VASCULAR FLOW

BACKGROUND OF THE INVENTION

1. Field of the Invention

The present invention relates generally to a device and method for accurately determining volumetric blood flow and, more particularly, to devices and methods utilizing ultrasonic transducer equipped arterial catheters configured to measure absolute or total vascular flow. The devices of the invention are particularly useful in measuring total pulmonary artery flow in segmental arteries, total main or segmental arterial and venous flow in other visceral organs, such as left or right main coronary, carotid, subclavian arteries or veins or renal blood flow in main or segmental arteries or veins.

2. Discussion of the Related Art

For many years diagnostic catheters have been available which measure cardiac output and pressures utilizing dye (contrast agent) dilution, thermodilution or oxygen consumption as the basis for measurement. More recently, catheters with more benign approaches have been developed which utilize Doppler ultrasonic transducers to measure instantaneous flow velocity in coronary and other arteries. These devices measure the Doppler shift or frequency modulation caused by the movement of blood cells within the blood vessel in known directional relation through an ultrasonic beam. In order for volumetric flow within the vessel of interest to be accurately determined utilizing such Doppler shift systems, however, such parameters or independent variables as the area of the vessel, velocity profile and the angle between the ultrasonic beam and the direction of flow must be determined and controlled with the required degree of accuracy.

One approach to the solution of this problem involves the use of a catheter device in which a relatively large, uniform beam of ultrasonic energy using a toroidal ultrasonic transducer carried by the catheter which emits a substantially uniform beam to illuminate the entire vessel of interest. This device attempts to make volumetric flow measurements independent of the size of the vessel, angle of incidence between flow and the ultrasonic beam, the velocity profile within the vessel, or the exact location of the transducer within the vessel. While such measurements are possible, the compromises involved reduce the precision and accuracy of the measurements below desired levels.

In addition, blood flow measuring catheter systems utilizing smaller single Doppler shift ultrasonic transducers have also been proposed. Examples of such devices which utilize the same ultrasonic transducer to measure both the diameter of the vessel of interest and the velocity of the blood cells flowing therethrough have also been proposed by Segal in U.S. Pat. Nos. 4,733,669 and 4,856,529. See also Segal et al "Instantaneous and Continuous Cardiac Output Obtained with a Doppler Pulmonary Artery Catheter", *Journal of the American College of Cardiology*, Vol. 13, No. 6, May 1989: 1382-92.

The accuracy of these devices depends on the precision of placement of the crystal in the lumen of the vessel of interest to achieve the proper known (assumed) angle between the direction of flow and the direction of the ultrasonic beam, and on the location of the ultrasonic transducer with respect to the wall of the vessel for accurate diameter determination. In addition, the crossection of the vessel must be assumed to be a constant function of the diameter.

Systems using multiple ultrasonic transducers in which one or more of such transducers are used to measure the flow velocity and one or more additional transducers are used to determine the diameter of the vessel of interest are illustrated and described by Nassi et al (U.S. Pat. Nos. 4,947,852 and 5,078,148). A Doppler pulmonary artery catheter using multiple transducers is illustrated and described by Segal et al in "Instantaneous and Continuous Cardiac Output in Humans Obtained with a Doppler Pulmonary Artery Catheter", *Journal of the American College of Cardiology*, Vol. 16, No. 6, Nov. 15, 1990:1398–407.

Other methods and ultrasonic devices based on the Doppler principle have been extensively applied in the measurement of coronary blood flow. For early use see, for example, Bing et al, "Techniques to Measure Coronary Blood Flow in Man", *American Journal of Cardiology*, Vol. 29, June, 1972:75–80 and Benchimol et al, "New Method to Measure Phasic Coronary Blood Velocity in Man", *American Heart Journal*, Vol. 81, No. 1, January, 1971:93–101. Devices of this type are described in Kohl et al, "The Pulsed Doppler Coronary Artery Catheter",*Circulation*, Vol. 56, No. 1, July 1977. A device for measuring blood flow and relatively small coronary artery branches is described by Wilson et al, "Transluminal Subselective Measurement of Coronary Artery Blood Flow Velocity and Vasodilator Reserve in Man", *Circulation*, Vol. 72, No. 1, July 1985:82–92. A steerable Doppler catheter having a central distal guidewire is described by Sibley et al in "Subselective Measurement of Coronary Blood Flow Velocity Using a Steerable Doppler Catheter", *Journal of the American College of Cardiology*, Vol. 8, No. 6, December 1986:1332–40.

While all of these prior devices and techniques have achieved a certain degree of success, each in its individual application, it is axiomatic that each also introduces certain measurement inaccuracies owing to the fact that certain assumptions must be made with respect to one or more independent variables involved in the volumetric flow calculations which are subject to time-variable changes. Thus, for example, one must assume that a vessel is always round or of constant crossection or that the ultrasonic transducer remains at a substantially constant angle with respect to the flow through the vessel of interest, etc. If dependence on a need to make any or all such assumptions in the determination can be eliminated, the accuracy and usefulness of such devices would be greatly enhanced.

There are many reasons why such measurements are important, and increased accuracies in them could provide valuable diagnostic tools in many areas. One important area in which the accurate measurement of absolute volumetric or total blood flow is important is in the evaluation of pulmonary hypertension. It is clinically important to know whether pulmonary hypertension is fixed or variable in those patients with primary or secondary pulmonary hypertension as well as pre- and post-cardiac and lung transplant patients and in those with adult respiratory distress syndrome.

In this regard, primary pulmonary hypertension is a serious and widespread condition which has been difficult to conclusively diagnose. The disease primarily affects small pulmonary arteries (40–300 $\mu$) resulting in intimal/medial hypertrophy fibrosis or subsequent loss of pulmonary capillaries. These histologic changes result in elevated pulmonary resistance leading to pulmonary hypertension. Pulmonary hypertension is a significant cause of morbidity and mortality in females between the ages of 20 and 40.

Prior to the present invention, it has been difficult to separate those patients with fixed and variable pulmonary hypertension. To this end, diagnostic trials have been instituted with various vasodilator drugs that include $PGI_2$, $PGE_2$, nifedipine, verapamil, hydralazine, nitroprusside, phentolamine, diazoxide, nitroglycerin, etc. Pulmonary resistance is calculated before the after administration of a vasodilating drug according to variations in electrical resistance measurements using thermodilution cardiac output and mean pulmonary artery (or pulmonary artery-wedge gradient) pressure. Even slight mistakes in measuring either of these two independent variables, however, results in significant error in calculation and inconclusive results. The primary reason for this effect apparently is that when a vasodilating drug is given systemically, it does not alter just the pulmonary vasculature, but it also affects systemic pre-load and after-load. Consequently, one may never be sure whether the measured drop in resistance is a consequence of reduced pulmonic pressure (secondary to systemic vasodilation), reduced cardiac contractility or increased cardiac output.

Furthermore, large amounts of the drug are required in these provocative studies, and this frequently makes the patient ill, at times resulting in significant morbidity and even death. This occurs as a consequence of dropping the systemic pressure in venous return to the right heart that is pumping against a fixed resistance in the pulmonary system.

There are many important advantages in being able to measure absolute segmental pulmonary artery flow as compared to measuring whole lung flow with thermodilution cardiac output. The ability to measure segmental flow with high accuracy would permit evaluation of regional changes in resistance while systemic hemodynamics remain unchanged. This isolation and localization means that only a fraction of the systemic vasodilating dose need be given into the distal vascular bed to measure reactivity. Thus, in this manner, the procedure would become a great deal safer inasmuch as it does not involve perturbing systemic hemodynamics with the vasodilator challenge.

It is further contemplated that catheters of the class would also be applicable to measuring absolute segmental visceral organ flow such as that pertaining to the renal, splenic and other arteries. In addition to local or segmental flow, absolute large vessel flow (i.e., subclavian artery, main renal artery, right coronary artery, left main and carotid artery flow, for example) would be readily measurable.

Accordingly, it is an object of the present invention to provide a self-aligning ultrasonic Doppler shift flow measuring catheter which measures absolute volumetric flow through a vascular lumen of interest.

It is a further object of the invention to provide a flexible ultrasonic Doppler flow catheter which eliminates the need for precisely posturing the catheter in the vessel of interest.

A still further object of the present invention is to obviate the need for measuring the diameter of the vessel of interest and/or estimating the crossectional area thereof.

Another object of the invention is the provision of a method and apparatus for measuring absolute large vessel flow.

Another object of the invention is the provisions of a method and apparatus to measure absolute segmental visceral organ blood flow.

These and other objects will become apparent based on the description and accounts of the invention including the detailed description and drawings below.

SUMMARY OF THE INVENTION

In accordance with the present invention, measurement of absolute or total volumetric blood flow in a vessel of interest is both simplified and made more accurate. The present invention provides a flexible catheter having a Doppler shift ultrasonic transducer fixed in position at a constant angle with respect to the velocity vector or direction of blood flow. This is done by incorporating it in a novel catheter design or approach in which a segment of a lumen of the catheter, at the time of the measurement, in effect, replaces a segment of the vessel whose absolute volumetric flow is to be determined.

In one embodiment, the device has inner flow obturator and flow-measurement catheters coaxially disposed, the flow-measurement catheter having inlet and outlet ports and a permanently mounted ultrasonic transducer system. With the inner catheter partially retracted and the distal tip of the flow-measurement catheter wedged in a vessel of interest, the full flow of blood in that vessel is routed through the distal tip section using the ports of the flow-measurement catheter. The blood flows past the ultrasonic transducer system and the absolute flow volume is measured with extreme accuracy. The distal tip section of the flow-measurement catheter is an open ended lumen which also is provided with a plurality of sidewall perfusion or flow ports spaced sufficiently proximal of the open distal end such that the ultrasonic transducer system can be mounted therebetween in fixed relation to the distal end of the catheter lumen segment and sufficiently downstream of the perfusion ports to enable a very accurate absolute instantaneous flow rate determination. The distal segment of the flow-measurement catheter lumen, then, acts as a short continuing channel or temporary replacement segment of the vessel of interest when the distal end of the outer catheter is wedged into the vessel of interest so that the total flow in the vessel passes between the perfusion ports and the distal lumen opening.

The inner obturator catheter has an outside diameter substantially coincident with the inside diameter of the lumen of the measurement catheter such that the obturator catheter can be readily passed longitudinally within the flow-measurement catheter; yet when the inner sleeve or inner catheter is advanced past the perfusion holes, occlusion occurs. Alternatively, an inner flotation catheter having an inflatable balloon can be used in which the balloon is inflated in the flow catheter just past the distal perfusion ports when occlusion of the ports is desired. The inner catheter extends the entire length of the flow-measurement catheter and is telescopingly mounted in the outer catheter lumen. The obturator catheter may have a pressure transducer mounted at or near the distal end thereof or be provided with an open lumen extending the length of the catheter which connects with a pressure monitor that can be utilized to evaluate the pressure or pressure wave form in the vessel and, with occlusion, confirm arterial wedge saturation.

As an alternative arrangement to the inner obturator catheter, the obturation device may be a coaxially mounted outer sleeve or sheath designed to slide longitudinally over the outside of the flow-measurement catheter lumen in this manner. This also accomplishes relative movement between the closure control device and the flow channel.

Once the inner (or outer) sleeve is pulled back or the balloon deflated, the perfusion holes cooperate with the distal opening in the outer or measuring catheter lumen to restore blood flow through the flow-measurement catheter lumen and over the ultrasonic Doppler transducer between the perfusion holes and the distal opening in the outer or measurement catheter lumen. In this manner, the distal segment of the outer catheter lumen functions as a segment of the vessel itself by carrying the total flow therethrough in a manner which causes very little pressure drop or flow perturbation. Turbulence and pressure loss can further be reduced by providing a total inlet port area that is at least twice the area of the corresponding outlet area. Flow entering the side port(s) and exiting the end port(s) is preferred; however, the reverse is also viable.

The ultrasonic Doppler crystal preferably is fixed in the wall of the outer or measurement catheter sufficiently distal of the perfusion ports and is mounted at a fixed, known distal or proximal directed angle with respect to the longitudinal access of the flow channel so that the direction of the ultrasonic beam is such that an accurate absolute measurement of volumetric flow through the center of the distal segment of the outer or measurement catheter is facilitated. The Doppler system may be operated in a steady state or pulsed mode. In the pulsed mode, the Doppler crystal alternately transmits and receives bursts of ultrasonic energy of a given repetitive frequency or sampling rate. In the steady state mode, the Doppler crystal is really, in effect, two crystals, one for transmitting and one for receiving.

The flow catheter, with the obturation device, can be positioned in the pulmonary or other artery or vessel of interest in the manner of any typical anglographic catheter. The inner catheter, if used, is preferably provided with a distal end port which can deliver a vasodilating drug, or other indicated medication, angiographic dye or any other material desired to be delivered to the measurement site. It can also contain or carry a pressure transducer to measure instantaneous pressure, if desired, or provide access to a remote pressure measurement device.

Further, with respect to the ultrasonic Doppler crystal, the only limitations with respect to placement of the crystal is that it be sufficiently separated from the perfusion ports to minimize turbulent effects and that, if forwardly directed, it be set far enough back from the distal opening of the catheter lumen so that the beam does not exit the distal end of the catheter at the fixed angle.

Although it can be of any convenient size, the thin walled outer measurement catheter is typically 6 to 9 French in diameter, has a flexible, thin wall and the catheter shaft and distal opening are typically at least 1.5 to 2.7 millimeters. The side ports are preferably oval in shape and elongated in the longitudinal direction. Side holes may also be provided in the distal end of the measurement catheter lumen. The diameter of the distal catheter lumen should approximate the diameter of the vessel or flow sought to be measured. The pulsed Doppler crystal natural output signal frequency is typically 5–30 Mhz and the crystal is mounted on the distal end of the lumen of the catheter approximately 2 to 3 millimeters from the distal end. If a continuous wave Doppler signal is used, the same general frequency range can be employed.

This concept can be employed to tailor catheters to measure absolute segmental visceral organ flow such as the renal and splenic arteries and, in addition, it can be provided with an occlusive cuff exterior to the distal end thereof adapted to function as an arterial sheath for measurement of large vessel flow such as that of the main renal artery, right coronary artery, left main and carotid artery.

DETAILED DESCRIPTION

Figure 1:
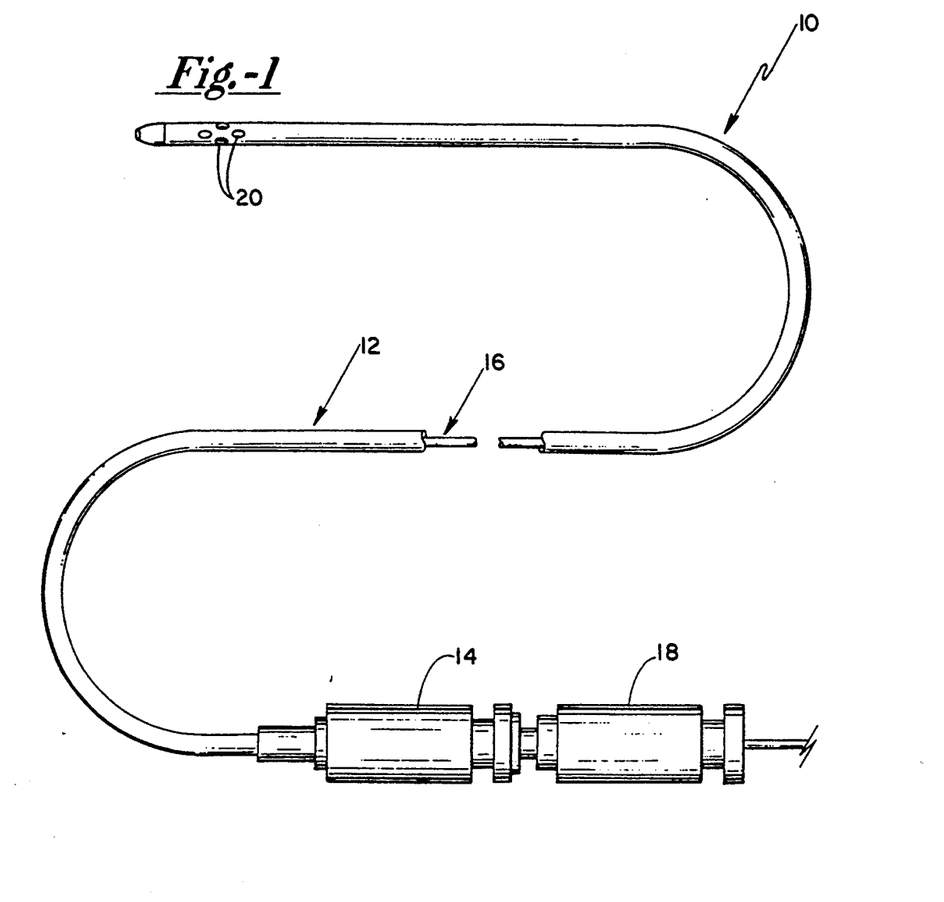
FIG. 1 is a schematic plan view with parts broken away of an embodiment of an angiographic catheter apparatus in accordance with the invention.

In accordance with the drawing Figures, a detailed description will next be presented. FIG. 1 depicts a co-axial dual angiographic catheter system designed to carry out the present invention. The catheter system is generally depicted by the numeral 10 and includes an outer or flow-measurement catheter 12 having a corresponding operational handle 14 and a coaxially disposed inner catheter 16 telescopically contained within the lumen of catheter 12 and having an operational handle 18. A plurality of proximal flow ports are shown at 20 and the inner catheter is depicted as protruding from the distal end of the measurement catheter. The flow-measurement catheter 12 can be of any desired diameter and is typically 6 to 9 French having a thin, flexible wall and a shape that is similar to a Stertzer-Myler PTCA guiding catheter, Cournand, multi-purpose Goodale-Lubin or other similar applicable catheter as would occur to those skilled in the art. The crystal may also be mounted on standard preformed angiographic catheters. For example, when measuring coronary flow, a standard Judkins style right or left coronary catheter may be adapted.

Figure 2:
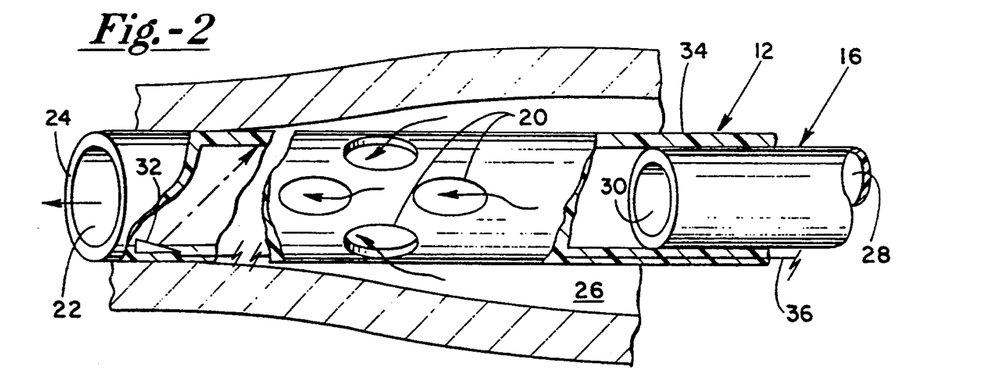
FIG. 2 is a greatly enlarged, fragmentary schematic view, partially in section, depicting the distal extremity of a catheter embodiment in accordance with FIG. 1 wedged in a vessel of interest.
Figure 3:
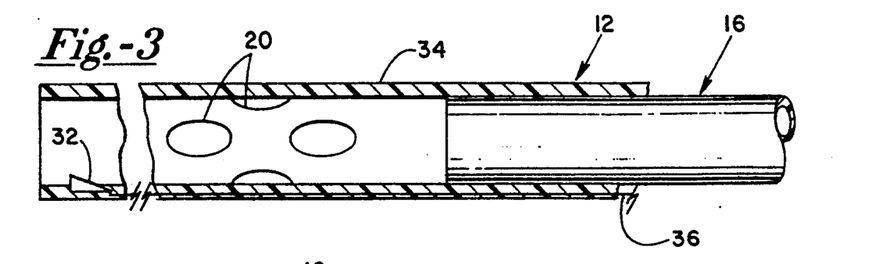
FIGS. 3 and 4 are fragmentary schematic views, partially in section, of the distal extremity of the catheter of FIG. 2 depicting alternate positions of the removable inner sleeve obturator catheter.

As better depicted in FIG. 2, the shaft of the flow-measurement catheter 12 is relatively thin walled and describes a relatively large diameter internal lumen 22 which continues and provides a rather large distal opening 24. The distal end of the catheter shaft 12 is depicted as being wedged in the vessel of interest 26. The coaxial inner catheter 16 is depicted as having a lumen 28 and an opening at the distal end 30.

Figure 4:
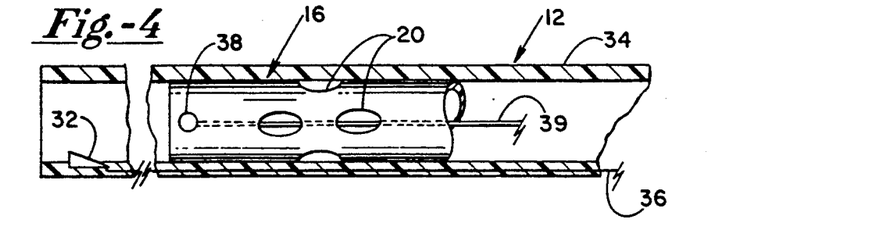

A piezoelectric Doppler crystal 32 is depicted mounted in the wall 34 of the flow-measurement catheter 12. The walls 34 of the distal segment of the catheter 12 are preferably quite thin so that the distal catheter lumen 22 approximates the internal diameter of the vessel 26 where the flow is to be measured. The outside diameter of the inner catheter 16 is such that the inner catheter 16 is just able to readily slide within the lumen 22 of the flow-measurement catheter 12 but also very close to the inner diameter of the lumen 22 in the vicinity of the perfusion ports 20 such that when the inner catheter is positioned as in FIG. 4, the flow into the lumen 22 via perfusion ports 20 is occluded.

In accordance with the present invention, it is desirable that perturbation of the normal natural blood flow through the vessel of interest be minimized commensurate with the desired accuracy of measurement results. Thus, as used for inlet ports, the perfusion ports 20 should collectively incorporate an area much larger than the distal opening 24 in the catheter lumen 22 (possibly 2-3 times the area) to minimize the system pressure drop. While perfusion ports of any geometry are within the parameters of the invention, it is generally preferred that the openings be relatively elongated in the direction of flow, and it has also been found that paired holes, slightly offset from each other on opposite sides of the catheter work quite successfully.

The Doppler crystal system may, for example, be one having natural frequency in the range of 5–30 mHz; but it must be capable of resolving velocity at the desired accuracy. The crystal illustrated is meant to include both single pulse operated transceiving crystals and also crystal system having simultaneous transmitting and receiving capabilities for continuous wave operation. The Doppler crystal is mounted on the distal inner lumen 22 of the catheter 12 the distance between the infusion ports 20 and the distal opening 24 such that the beam will accurately measure the blood cell particle velocity.

Figure 10:
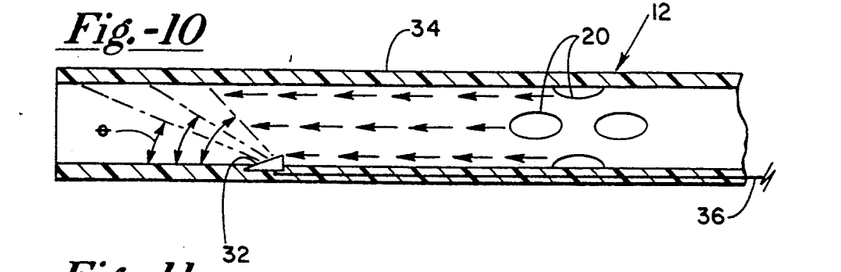
FIGS. 10 and 11 are fragmentary, broken, schematic views, partially in section, of the distal extremity of the outer catheter of the invention illustrating transducer placement.
Figure 11:
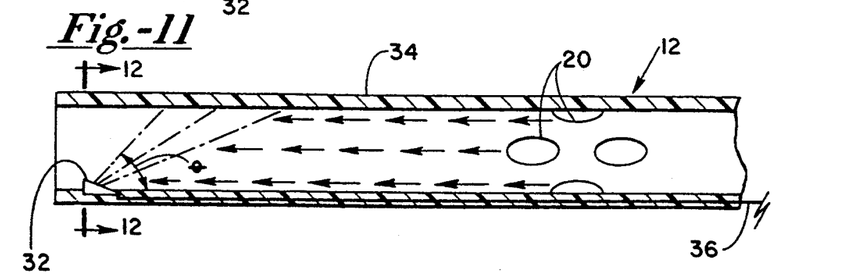
Figure 12:
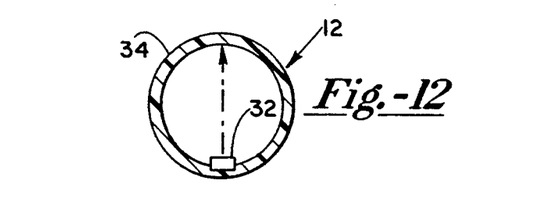
FIG. 12 is a sectional view taken along 12—12 of FIG. 11.

As illustrated in FIGS. 10–12 the crystal can be pointed or aimed in either the distal or proximal direction, the only limitations being that the crystal be set back far enough from the distal end so that, at the angle the crystal is mounted, the beam does not exit the distal end of the catheter and that the ultrasonic beam traverses the center of the catheter lumen to provide an accurate velocity profile as shown in the sectional view of FIG. 12. The Doppler crystal is mounted at a fixed angle normally such that the beam subtends an angle $\theta$ between about 10 degrees and 60 degrees with the longitudinal axis of the catheter 12 or the direction of the velocity vector of flow. The exact angle, of course, is not critical as long as the flowing stream is traversed in the manner described.

The crystal can be mounted on a platform and inserted through a hole in the catheter near the distal end if it is desired to repeatably fix the crystal angle with reference to the lumen of the catheter. One or more lead wires 36 are provided to connect the crystal system with the catheter handle to energize and receive signals, alternately or simultaneously depending on operative mode, between the handle and the stream to be measured through the crystal system. It is preferred that the crystal be at least partially recessed into the wall 34 to minimize flow perturbation, and mounting the crystal flush with the interior wall of the lumen 22 is most preferred.

The insulated electrical connectors 36 may run along the outside of or be embedded in the catheter wall 34 as desired. Preferably, however, the connector or connectors from the Doppler crystal are run along the outside of the catheter 12 and covered over with an amount of suitable benign insulating material such as epoxy to fix the wires to the catheter wall and, at the same time, provide insulation for the conductors. Alternatively, of course, the wires can be run in an internal parallel lumen as long as the main lumen is of the appropriate diameter. The wires should be 5–10 centimeters longer than the catheter for ready external connection.

A variety of functions may be incorporated in the inner catheter 16 with respect to the measurement made by the catheter system of the invention. The proximal hub 18 (FIG. 1) is connected to a pressure monitor (not shown) in a conventional manner to monitor the pressure in the vessel of interest to verify proper location of the catheter in the vascular system and, also to verify the obturation of flow when the inner catheter is advanced to close the flow through the ports 20. A pressure transducer can also be carried close to the distal end of the inner catheter as at 38 with lead 39 in FIG. 4. This mode will also confirm the location or wedge occlusion of the outer catheter in the vessel of interest based on the pressure wave signal received through the lumen of the inner catheter.

Figure 5:
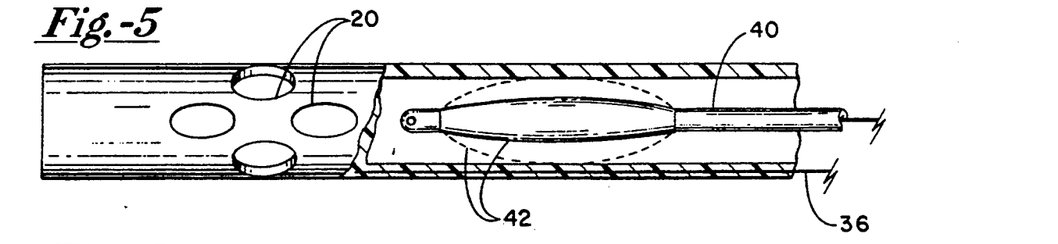
FIG. 5 is a greatly enlarged, fragmentary schematic view, partially in section, of the distal extremity of an alternative embodiment of the catheter of FIG. 1 utilizing an inner flotation catheter with an occlusive balloon.

As shown in FIG. 5, the inner catheter can also be in the form of a floatation catheter 40 in which a sealing balloon 42 is inflated through a second internal catheter lumen (not shown) in a well-known manner when it is desired to occlude the flow through the ports 20. Such a catheter, of course, is much easier to move within the lumen 22 of the flow-measurement catheter 12; and when the balloon is deflated, this design facilitates placement of the catheter in the vessel of interest without the need for fluoroscopic visualization.

Figure 6:
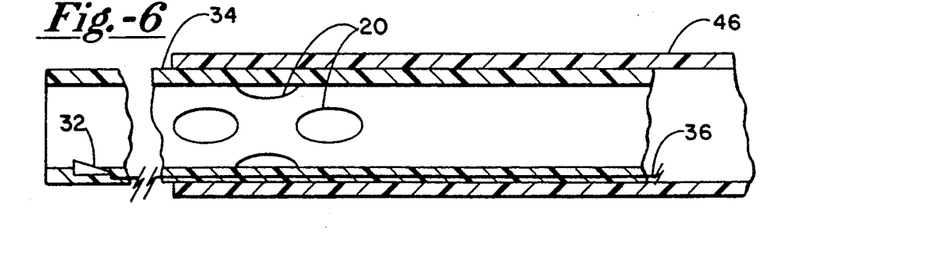
FIGS. 6 and 7 are fragmentary schematic views, partially in section, of the distal extremity of an alternate embodiment of the catheter employing an outer obturation sleeve.
Figure 7:
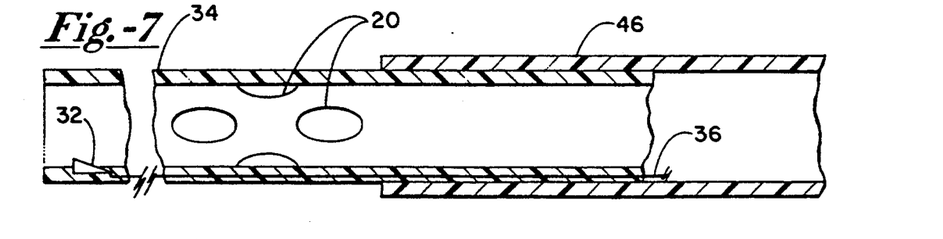

As further illustrated in FIGS. 6 and 7, a further important alternative embodiment for the obturation means for the perfusion ports 20 of the flow-measurement catheter 12 is illustrated in the form of a coaxially mounted outer sleeve or sheath member 46 which is freely longitudinally adjustable with respect to the outer wall 34 of the flow-measurement catheter 12. This represents another method of opening and closing the access to the perfusion ports which can be employed. The use of the outer catheter sleeve or sheath member 46 may, however, reduce the allowable diameter of the flow-measurement catheter 12 and so its interior lumen 22 but may present advantages for certain applications of the system. FIG. 7 is a drawing similar to FIG. 6 showing the sleeve 46 retracted beyond the perfusion ports 20 thereby restoring flow to the system.

Using a segmental pulmonary artery branch as an example, in operation, the flow catheter, with the inner sleeve covering the infusion port openings, is positioned in the pulmonary artery in the usual fashion. The catheter is then wedged into the distal pulmonary artery.

Since the inner sleeve is advanced past the perfusion holes, wedge occlusion can be confirmed by evaluating the monitored pressure wave form as well as having the option to confirm the catheter's wedge position by obtaining a pulmonary arterial wedge saturation. If an inner flotation catheter is used, the balloon is inflated, in the flow catheter, just past the distal perfusion ports. Pulmonary artery wedge pressures can then be sampled via the inner flotation catheter's lumen or using another transducer.

Once the catheter is adequately wedged, the inner (or outer) sleeve is retracted or pulled back proximal to the perfusion holes in the catheter wall. Functionally, this reroutes the blood flow into the catheter's lumen, over the Doppler crystal and out the distal end, returning once again to the artery.

Since the angle of incidence and cross sectional area are known a priori, and the velocity shift measured, a very accurate absolute volumetric flow measurement can be calculated. The cross sectional area of the perfusion holes in the shaft of the catheter are deliberately much greater than the distal opening, thus there is no significant pressure drop across the catheter segment. Furthermore, since the Doppler catheter is wedged into a distal segmental pulmonary artery, the catheter is closely matched to the surrounding vessel wall. Thus, the catheter functions as a continuation of the vessel.

Figure 8:
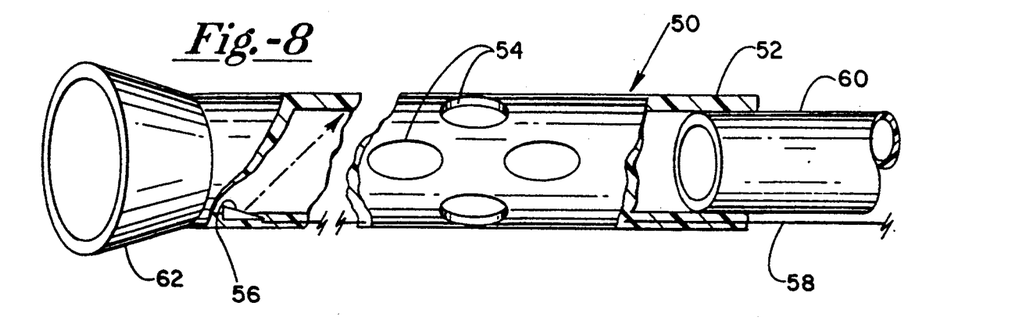
FIGS. 8 and 9 are fragmentary schematic views, partially in section, of the distal extremity of alternative catheter embodiments with types of arterial ostia seals.
Figure 9:
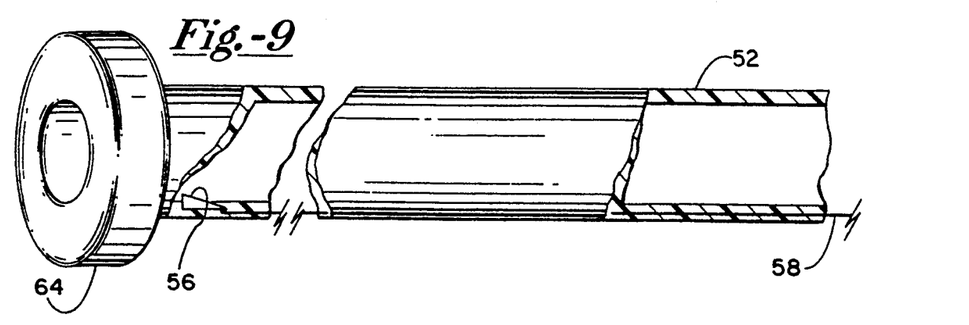

Catheter devices of the class of the invention, with minor modifications, can be employed to measure absolute segmental visceral organ flow such vessels as the renal and splenic arteries. Furthermore, absolute large vessel flow (i.e., subclavian, main renal artery, right coronary artery, left main and carotid artery flows) can be measured. Such a modified device is shown in FIGS. 8 and 9, in which a flexible right angle bend (not shown) is put in an outer catheter 50 having a wall 52 and being provided with a plurality of infusion ports 54, an ultrasonic piezoelectric transducer crystal 56 with electrical connectors 58 and an inner or sleeve catheter 60 in the lumen 60 of the catheter 50. The distal extremity of the catheter 50 is provided with a soft latex-like "funnel" member 62 which may be conveniently molded to the tip of the catheter. The funnel member 62 operates to occlude the ostia of the large vessel of interest and thereby ensure that no extraneous flow bypasses the Doppler crystal 56. As with the other embodiments, the maximum diameter of the funnel 62 should correspond to the maximal ostium encountered. Thus, for the left main artery, the maximal funnel diameter may be as big as 5 to 6 millimeters, and for the right coronary artery diameter of 4 millimeters should suffice.

Of course, the size of the funnel may present certain problems or difficulties when it comes to insertion into the arterial sheath of the catheter since the sheath is normally no more than 3 millimeters OD. Several approaches can be used to meet this problem including inserting the funnel folded over length wise just enough to advance it through the sheath. Once in the iliac or larger arterial vessels moving the catheter should not be a problem. The relatively tight fitting plastic sleeve (FIGS. 6 and 7) can be slid over the flow measuring catheter to also compress the funnel. This sheath will straighten the funnel so that it may be inserted atraumatically through the sheath and advanced into the appropriate position. When in position, the sheath can be pulled back, and the funnel is allowed to expand to its full dimension.

FIG. 9 illustrates an alternate large vessel adaptation in which extraneous circumvented blood flow is protected by the provision of a coaxial plastic lumen extruded over the body of the catheter and formed into an inflatable and very compliant balloon structure 64 which is similar to a Swan Ganz hemodynamic or Berman angiographic monitoring catheter. Once the catheter has been engaged in the vascular site, the balloon 64 is slowly inflated until a damped or end pressure (ventricularized) wave form is seen. This wave form will ensure that nearly all of the flow has been redirected through the catheter.

In addition, it should be noted with respect to the inner catheter in all such systems that it also can be used to administer dosages of any type of medication, vasodilator drugs, antibiotic drugs, contrast agents, or the like. Contrast agents, such as various dyes, may also be utilized to determine or confirm the absence of leakage around the outer catheter tip, i.e., verifying that the distal end of the outer catheter is wedged into the vessel of interest.

Although it is most desirable to have each crystal mounted at a precise and known angle, this may represent a significant engineering challenge. If this cannot be accomplished in a cost effective method, then there is a relatively simple way around this issue. In-vitro calibration can be performed at the factory, before or after the procedure. One method involves infusing a measured amount of fluid or blood over a timed period through the flow-measurement catheter while operating the Doppler system. The actual flow is then compared with that measured by the Doppler system and the ratio of the observed to the measured flow yields a correction factor which may thereafter be applied to in vivo measurements. If desired, such measurements may be made at several different flow rates and a correction curve developed. Normally, however, such a curve would be substantially linear in a relevant flow range.

Calibration can also be accomplished by covering the side ports from the outside of the catheter, and providing a known volume of blood (or test solution of similar viscosity) by injection through the catheter at a known flowrate. (Alternatively, the catheter can be hooked up to an arterial or venous catheter and a timed collection obtained.) During this time, the Doppler is operated and the velocity shift is recorded. Working backward from the Doppler and Continuity equations, it is easy to calculate the cosine of the Doppler angle $\theta$ and derive a correction factor:

$$i.e.,\ F = 2F_o * V * \cos \theta / C$$

where
 F=Frequency shift
 $F_o$=Carrying frequency=20 mHz
 V=Velocity
 C=Speed of sound in blood=1580 cm/sec
 CSA=Cross sectional area
 thus V=F*C / 2$F_o$ Cos $\theta$ V
 then V*CSA of catheter=Observed flow
 Measured/Observed=correction factor Thus, an exact mounting of the crystal, while desirable, is not critical.

The purpose of the inner (or outer) sleeve is only to occlude the perfusion ports which are situated behind the Doppler crystals and to transmit pressure signals and materials via the lumen therefor. The sleeve need not extend past the crystal. However, an alternate design is to construct the sleeve so that it concentrically begins to taper to a smaller I.D., i.e., 7-4 French, immediately after the last perfusion port. Thus, there is a good deal of clearance between the crystal and the sleeve, and the crystal is never in jeopardy of being bumped.

With respect to the operation of the Doppler crystal system, the velocity of the flow encountered for most applications of the system is such that a single crystal pulsed Doppler system will produce excellent results with no fear of aliasing. At higher velocity flow rates, however, boundary conditions may be reached which involve Nyquist stability criteria. This occurs when the beat frequency between the signal frequency and the sampling frequency is such that it is susceptible to misinterpretation, i.e., to result in a false signal which yields an ambiguity with respect to flow direction sensed by the Doppler crystal system. Such criteria are well known in the fluid flow arts and, in these cases, associated aliasing problems can readily be solved by the use of a Doppler crystal system operated in a continuous wave or non-pulsed mode. This requires the crystals 32 to be dual crystals or at least be dual function crystals, i.e., have the ability to receive echo signals as well as to transmit so that both functions can be accomplished simultaneously in the continuous signal wave read by the receiver.

Such problems are associated with very high blood flow velocity. Very high flow velocity is particularly likely when the flow-measurement catheter is wedged close to a vascular stenosis where significant cross sectional blockage requires the blood to flow at a higher velocity to allow enough volume past the constriction.

The precise means of measuring and calculating velocity measurements are well known in the fluid flow art and, it is believed, need not be discussed in great detail here. One method of measurement includes the application of zero crossing measurement devices to the received signals in a well-known manner. Where additional accuracy is required, Laplace or Fourier transforms may be used to solve high order equations involving spectral analysis to calculate the flowrate as a function of the frequency. These methods, while complex, are well known to those skilled in the art and need no further explanation here.

The technique of total flow diversion with minimal perturbation or interruption of normal vascular flow which also determines the velocity vector of blood flow with respect to the Doppler crystal makes the flow measurements according to the present invention relatively error free and clearly related to total stream flow.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A catheter for measuring total volumetric vascular flow at a location in a vessel of interest comprising:

(a) a flow-measurement catheter including a relatively long, hollow tubular member having distal and proximal ends and describing a continuous lumen having a distal measurement lumen segment of known geometric cross section, the distal end of the distal segment of the lumen having one or more end access ports and one or more sidewall access ports at a point close to but spaced from the distal end thereof and providing side access to the interior of the measurement lumen, the measurement lumen thereby being capable of carrying the full flow of the vessel of interest between the one or more end ports and the one or more side access ports when the catheter is situated at the location of interest, the flow-measurement catheter further extending into and being sealably connected to a handle means at the proximal end thereof;

(b) an obturator catheter comprising a relatively long, hollow tubular member having a distal and a proximal end and describing a continuous lumen therein and further being designed to be coaxially combined with the flow-measurement catheter and be longitudinally movable with respect to the flow-measurement catheter, the obturator catheter having the ability to occlude the one or more sidewall access ports in the flow-measurement catheter sidewall when the distal end of the obturator catheter is advanced so as to cover the one or more sidewall ports in the flow-measurement catheter;

(c) transducer means associated with the distal measurement segment of the flow-measurement catheter means for generating and receiving a beam of ultrasonic energy in the lumen of the outer catheter, the transducer means being disposed in fixed relation to the longitudinal axis of the distal measurement segment of the lumen of the flow-measurement catheter such that the total volumetric blood flow between the one or more side access ports and the one or more distal end access ports in the flow-measurement catheter lumen can be accurately sensed;

(d) means for energizing and communicating with the transducer means.

2. The apparatus of claim 1 wherein the total cross sectional area of the one or more side access ports and the one or more end access ports are such that for a given flow direction therebetween, the ports serving as inlets have a greater total cross section than those serving as outlets.

3. The apparatus of claim 1 wherein the flow enters through the one or more side ports and exits through the one or more end access ports.

4. The apparatus of claim 3 wherein the area of the sidewall access ports is at least double that of the one or more end access ports.

5. The apparatus of claim 4 wherein the sidewall access ports are elongated with respect to the longitudinal axis of the flow-measurement catheter.

6. The apparatus of claim 3 wherein the sidewall access ports are elongated with respect to the longitudinal axis of the flow-measurement catheter.

7. The apparatus of claim 3 wherein one or more end access ports is an open end.

8. The vascular flow measurement apparatus of claim 7:

(a) wherein the flow enters through the one or more side ports and exists through the one or more end access ports;

(b) wherein the area of the sidewall access ports is at least double that of the one or more end access ports;

(c) wherein the sidewall access ports are elongated with respect to the longitudinal axis of the flow-measurement catheter; and (d) wherein the one or more end access ports is an open end.

9. The apparatus of claim 1 further comprising pressure transducing means for communicating the static pressure profile from within the measurement catheter lumen.

10. The apparatus of claim 1 further comprising arterial ostia sealing means on the external surface of the distal portion of the measuring catheter to seal the vascular ostia about the measurement catheter when it is used to measure the total flow in a vessel at a location where the vessel has an internal cross sectional area larger than the external cross sectional area of the measurement catheter.

11. The apparatus of claim 10 wherein the ostia seal is in the form of an external collar of resilient compatible material.

12. The apparatus of claim 10 wherein the ostia sealing means is in the form of a circumferentially inflatable resilient balloon member.

13. A vascular flow measurement catheter device for measuring total volumetric flow through a vessel of interest comprising:

(a) a flow-measurement catheter means including a full flow lumen of known cross sectional geometry having a relatively short distal measurement segment provided with inlet and outlet ports positioned to carry the full flow of the vessel of interest in the manner of a segment of the vessel itself when the flow-measurement catheter means is positioned in the vessel of interest;

(b) an inner obturator means in coaxially disposed relation to the full flow lumen of the flow-measurement catheter and adapted to travel along and within the full flow lumen of the measurement catheter, the obturator means shutting off the flow through the measurement catheter when advanced over the inlet or outlet ports of the measurement catheter;

(c) ultrasonic transducing means associated with the flow-measurement catheter means for communicating the velocity of the fluid in the measurement segment of the full flow lumen; and (d) means for determining the total volumetric flow in the measurement segment of the measurement catheter lumen.

14. The vascular flow measurement apparatus of claim 13 wherein the inlet port or ports have a greater total cross sectional area than the outlet port or ports.

15. The vascular flow measurement apparatus of claim 14:

(a) wherein the flow enters through the one or more side ports and exits through the one or more distal end ports;

(b) wherein the area of the sidewall access ports is at least double that of the distal end port; and (c) wherein the sidewall access ports are elongated with respect to the longitudinal axis of the flow-measurement catheter.

16. A vascular flow measurement catheter device for measuring total volumetric flow through a vessel of interest comprising:

(a) a flow-measurement catheter means including a full flow lumen of known cross sectional geometry having a relatively short distal measurement segment provided with inlet and outlet ports positioned to carry the full flow of the vessel of interest in the manner of a segment of the vessel itself when the flow-measurement catheter means is positioned in the vessel of interest;

(b) an outer obturation sleeve in coaxially disposed relation to the flow-measurement catheter and adapted to travel along the outside thereof, the obturation sleeve shutting off the flow through the measurement catheter when advanced over the inlet or outlet ports;

(c) ultrasonic transducing means associated with the flow-measurement catheter means for communicating the velocity of the fluid in the measurement segment of the full flow lumen; and (d) means for determining the total volumetric flow in the measurement segment of the measurement catheter lumen.

17. The vascular flow measurement apparatus of claim 16 wherein the inlet port or ports have a greater total cross sectional area than the outlet port or ports.

18. The vascular flow measurement apparatus of claim 17:

(a) wherein the flow enters through the one or more side ports and exits through the one or more end access ports; and (b) wherein the area of the sidewall access ports is at least double that of the one or more end access ports; and (c) wherein the sidewall access ports are elongated with respect to the longitudinal axis of the flow-measurement catheter.

19. The vascular flow measurement apparatus of claim 17:

(a) wherein the flow enters through the one or more side ports and exits through the one or more end access ports;

(b) wherein the area of the sidewall access ports is at least double that of the one or more end access ports;

(c) wherein the sidewall access ports are elongated with respect to the longitudinal axis of the flow-measurement catheter; and (d) wherein the one or more end access ports is an open end.

20. A method of measuring total volumetric flow at a particular location in a vessel of interest comprising the steps of:

(a) introducing within the vessel of interest a flow-measurement catheter system having a distal end and having a flow-measurement lumen of known cross sectional geometry, the flow-measurement lumen being provided with one or more inlet and outlet ports configured to carry the entire flow of the vessel of interest, the flow-measurement catheter system carrying an ultrasonic transducer means mounted therein and disposed to measure the flow velocity therethrough, the flow-measurement catheter system further having obturation means axially adjustable with respect to the flow-measurement lumen to occlude one or more of said one or more inlet ports;

(b) positioning the flow-measurement catheter system within the vessel of interest as desired for flow measurement;

(c) axially adjusting the obturation means, as necessary, to allow the full flow of the vessel of interest to enter the flow-measurement lumen;

(d) using the ultrasonic transducer means and the known geometry of the catheter lumen to measure the volumetric flow rate through the vessel of interest.

21. The method of claim 20 wherein the ultrasonic transducer is operated in a pulsed mode.

22. The method of claim 20 wherein the ultrasonic transducer means is operated in a continuous mode.

23. The method of claim 20 wherein the ultrasonic transducer means is pre-calibrated based on a known volumetric flow.

24. The method of claim 20 wherein the flow-measurement catheter further comprises pressure transducer means for monitoring pressure within the flow-measurement lumen and further comprising the step of monitoring the pressure wave form.

25. The method of claim 24 wherein the vessel of interest is the pulmonary artery, wherein the flow-measurement catheter system is positioned by wedging the distal end into the distal pulmonary artery, and including the further step of confirming wedge occlusion by evaluating the monitored pressure wave form.

* * * * *